United States Patent [19]

Hufton et al.

[11] Patent Number: 4,599,888
[45] Date of Patent: Jul. 15, 1986

[54] AIR BUBBLE DETECTOR DEVICE

[75] Inventors: Arthur Hufton, Mobile, Ala.; David Gardner, Halse, United Kingdom

[73] Assignee: Teledyne Industries, Inc., Los Angeles, Calif.

[21] Appl. No.: 558,979

[22] Filed: Dec. 7, 1983

[51] Int. Cl.$^4$ .............................. G01N 7/00
[52] U.S. Cl. .................... 73/19; 324/61 R; 324/65 R
[58] Field of Search .............. 73/53, 19, 64; 324/65 R, 61 R, 61 P

[56] References Cited

U.S. PATENT DOCUMENTS

| 2,720,624 | 10/1955 | Gunst et al. | 324/61 R |
| 3,114,257 | 12/1963 | Foster et al. | 324/61 R |
| 3,192,473 | 6/1965 | Marsh | 324/61 R |

FOREIGN PATENT DOCUMENTS

| 104243 | 8/1981 | Japan | 324/61 R |
| 572696 | 9/1977 | U.S.S.R. | 324/61 R |

Primary Examiner—Bernard Nozick
Attorney, Agent, or Firm—Gifford, Groh, VanOphem, Sheridan, Sprinkle & Dolgorukov

[57] ABSTRACT

A device is provided for detection of presence of air within a fluid system containing a dielectric fluid, such as oil. The device comprises a capacitor having a tubular capacitor plate which is connected in series with the fluid system. An elongated cylindrical capacitor plate is coaxially secured within the tube by disc shaped spacers constructed of an electrical insulating material. Both the first and second contacts are connected to an oscillator having a frequency dependent upon the capacitance of the capacitor. The capacitance of the capacitor varies in an amount proportional to the amount of air contained within the dielectric fluid to thereby vary the frequency of the oscillator. The frequency output from the oscillator is connected to an indicator circuit to provide an indication of the oscillator frequency and thus of the amount of air within the dielectric fluid.

4 Claims, 2 Drawing Figures

AIR BUBBLE DETECTOR DEVICE

BACKGROUND OF THE INVENTION

I. Field of the Invention

The present invention provides a device for detecting the presence of air bubbles within a dielectric fluid, such as oil.

II. Description of the Prior Art

In engine lubrication systems, the presence of air entrained within the lubricant can result in improper or inadequate lubrication of the engine components. The improper or inadequate lubrication of the engine components, in turn, can result in damage to the engine components as well as cavitation of the lubricant pump.

Many engine lubrication systems include an oil pressure transducer which monitors the oil pressure from the oil pump and alerts the engine operator when the oil pressure falls below a predetermined amount. These previously known oil pressure transducers, however, are incapable of detecting the presence of entrained air within the oil lubrication system. Consequently, even though the oil pressure may be adequate, the presence of entrained air within the oil may nevertheless result in damage or excessive wear of the engine components.

SUMMARY OF THE PRESENT INVENTION

The present invention provides a device which detects the presence and amount of entrained air within a dielectric fluid, such as oil.

In brief, the device of the present invention comprises a capacitor having a first and second capacitor plate. The first capacitor plate is tubular and cylindrical in shape and is secured in series with the oil lubrication system for the engine. The second capacitor plate is elongated and generally cylindrical in shape and is coaxially mounted within the first contact by spacing members. The spacing members are generally disc shaped and constructed of an electrical insulating material thus insulating the first and second capacitor plates from each other. In addition, a plurality of openings are formed through the spacing members which enable the lubricant or oil to flow substantially unimpeded through the capacitor.

The capacitor plates are, in turn, secured to and form a part of an electronic oscillator which oscillates at a frequency dependent upon the capacitance of the capacitor. Consequently, a change of the capacitance of the capacitor, as would occur during the presence of air within the lubricant, varies the frequency of the oscillator. The frequency output from the oscillator provides an input signal to a circuit which indicates the frequency of the oscillator and thus the amount of air within the oil.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
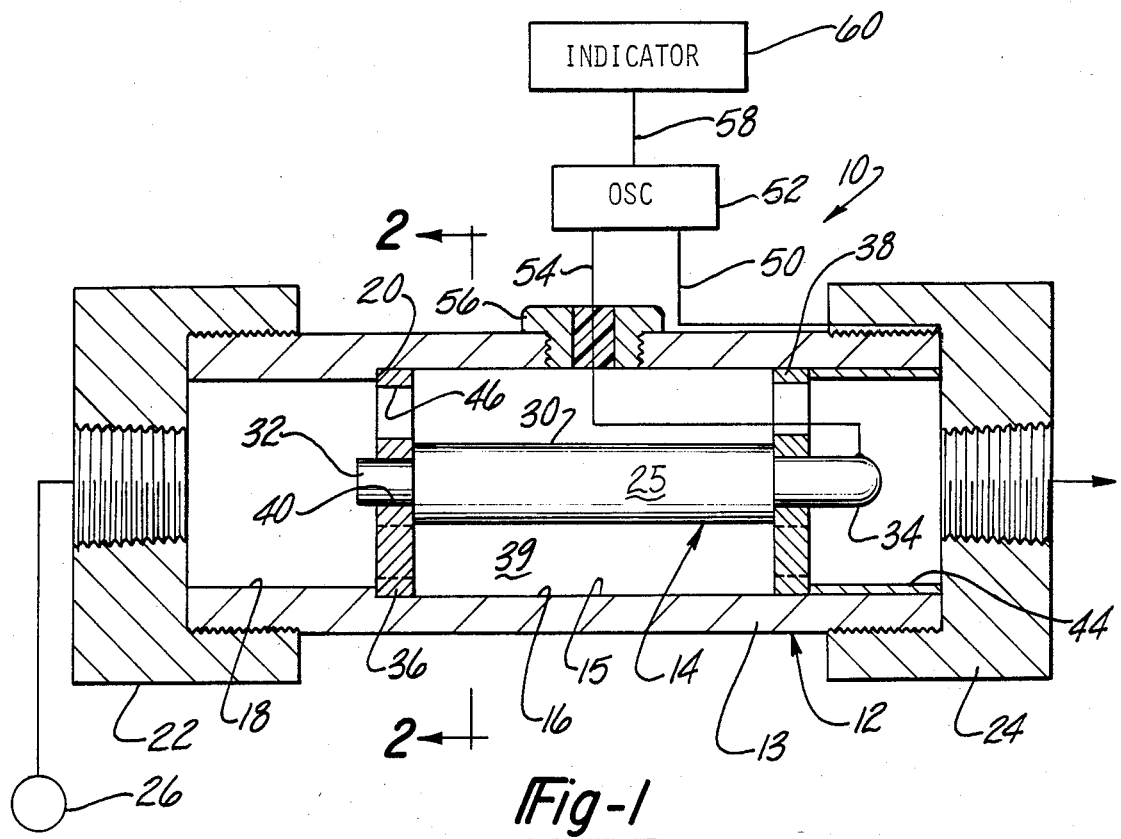
FIG. 1 is a longitudinal sectional view illustrating a preferred embodiment of the present invention.
Figure 2:
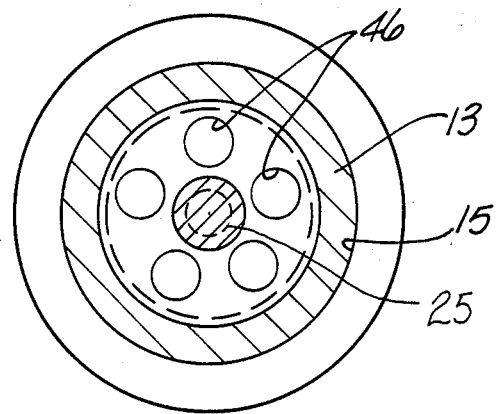
FIG. 2 is a cross sectional view taken substantially along line 2—2 in FIG. 1.

With reference to the drawing, a preferred embodiment of the present invention is thereshown and comprises a capacitor plate 10 having a first capacitor plate 12 and a second capacitor 14. The capacitor plates 12 and 14 are constructed of a suitable metallic material, such as copper.

The first capacitor plate 12 comprises a generally tubular and cylindrical tube 15 having a cylindrical inner periphery 16. A radially reduced diameter portion 18 at one end of the tube 15 forms an annular shoulder 20 within the interior of the tube 15 for a reason to be subsequently described.

A first and second end cap 22 and 24, respectively, threadably engage opposite ends of the tube 15 and fluidly secure the tube 15 in series with a dielectric fluid system 26, such as an engine lubrication system. The end caps 22 and 24 comprise conventional fluid fittings.

The second capacitor plate 14 comprises a rod 25 having a cylindrical midportion 30 and reduced diameter portions 32 and 34 at each end. The rod 25 is coaxially mounted within the interior of the tube 15 by two disc shaped spacing members 36 and 38 thus forming a chamber 39 therebetween which is open to the fluid system 26.

The spacing members 36 and 38 are substantially identical to each other and have a diameter substantially the same as the internal diameter of the tube 15. Each spacing member 36 and 38 includes a central through-bore 40 into which the reduced diameter ends 32 and 34 of the second capacitor plate 14 are inserted so that the rod midportion 30 is entrapped between the spacing members 36 and 38.

The first spacing member 36 is inserted into the interior of the tube 15 until it abuts against the shoulder 20. The rod 25 and second spacing member 38 are then inserted into the tube 15. Finally, a cylindrical sleeve 44 is sandwiched between the end cap 24 and the second spacing member 38 thus locking the rod 25 between the spacing members 36 and 38 and coaxial with the tube 15. Each spacing member 36 and 38 also includes a plurality of openings 46 which enable fluid flow from one end of the tube 15 and to the other.

With reference now particularly to FIG. 1, a first electrical wire 50 is electrically secured to the first capacitor plate 12 in any conventional fashion. However, as shown, the wire 50 is entrapped between the sleeve 44 and the inside of the tube 15. This electrical wire 50 is electrically connected to and forms a part of an oscillator circuit 52.

A second electrical wire 54 is secured at one end in any conventional fashion to the second capacitor plate 14 or rod 25 and, at its other end, to the oscillator circuit 52. The wire 54 is electrically insulated from the tube 15 in any conventional fashion, such as an electrical insulator plug 56.

With the capacitor plates 12 and 14 electrically connected to the oscillator 52, the capacitor formed by the plates 12 and 14 form a part of the oscillator circuit 52. The oscillator circuit 52 generates an output frequency on an output line 58 which is proportional to the capacitance of the capacitor 10. The output line 58 from the oscillator circuit 52 in turn forms an input signal to an indicator circuit 60 which provides an indication of the oscillator frequency and thus of the capacitance of the capacitor 10.

In operation, and assuming that the tube 15 is completely filled with a dielectric fluid, such as oil, the capacitor 10 will have a predetermined capacitance so that the oscillator circuit 52 oscillates at a predetermined frequency. Conversely, entrained air within the fluid in the tube 15 varies the capacitance of the capacitor 10 in an amount proportional to the amount of entrained air. Consequently, the entrained air within the fluid varies the capacitance of the capacitor 10 and, correspondingly, the frequency of the oscillator 52. A variation of the frequency of the oscillator circuit 52 is displayed to the user by the indicator circuit 60 thus alerting the operator of both the presence and amount of air within the fluid.

From the foregoing, it can be seen that the device of the present invention provides a simple, inexpensive and yet totally effective means for detecting the presence and amount of entrained air within a dielectric fluid, such as oil. Furthermore, such entrained air will be detected regardless of the oil pressure or oil flow rate.

Having described our invention, however, many modifications thereto will become apparent to those skilled in the art to which it pertains without deviation from the spirit of the invention as defined by the scope of the appended claims.

We claim:

1. A device for detecting the presence of air in a fluid system containing a dielectric fluid, comprising:

a capacitor comprising a first electrical plate comprising a tube, a second electrical plate comprising a rod, and means for coaxially mounting said rod in said tube, said plates being spaced apart from each other and defining a continuous cylindrical chamber therebetween;

means for fluidly connecting said chamber to said fluid system; and means for determining the capacitance of said capacitor, comprising an oscillator, said oscillator including said capacitor as an element so that a variation of the capacitance of said capacitor varies the frequency of said oscillator, wherein said mounting means comprises a pair of discs, each disc constructed of an electrically insulating material and having an axial hole and a further hole spaced from said axial hole, said discs being positioned within said tube so that an outer periphery of each disc engages an inner periphery of said tube at axially spaced positions and said rod being positioned in said discs' axial holes.

2. The invention according to claim 1, wherein said tube comprises a shoulder, and wherein one of said disks is abuttable against said shoulder.

3. The invention according to claim 1, wherein said tube is capped by an end cap, and wherein said device additionally comprises an annular spacer disposed between and abutting said end cap and one of said disks.

4. The invention as defined in claim 1 wherein said rod includes a reduced diameter portion at each end.

* * * * *